United States Patent
Kim et al.

(10) Patent No.: US 9,322,032 B2
(45) Date of Patent: Apr. 26, 2016

(54) *ARABIDOPSIS* RING E3 UBIQUITIN LIGASE FOR PROMOTION OF PLANT GERMINATION

(75) Inventors: Woo Taek Kim, Goyang-si (KR); Moon Young Ryu, Seoul (KR); Seok Keun Cho, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 20 days.

(21) Appl. No.: 14/122,031

(22) PCT Filed: Aug. 22, 2011

(86) PCT No.: PCT/KR2011/006187
§ 371 (c)(1),
(2), (4) Date: Nov. 25, 2013

(87) PCT Pub. No.: WO2012/165714
PCT Pub. Date: Dec. 6, 2012

(65) Prior Publication Data
US 2014/0245492 A1 Aug. 28, 2014

(30) Foreign Application Priority Data

May 27, 2011 (KR) .................. 10-2011-0050802

(51) Int. Cl.
*C12N 15/82* (2006.01)
*C07K 14/415* (2006.01)

(52) U.S. Cl.
CPC .......... *C12N 15/8273* (2013.01); *C07K 14/415* (2013.01); *C12N 15/8271* (2013.01); *C12N 15/8293* (2013.01)

(58) Field of Classification Search
None
See application file for complete search history.

(56) References Cited

U.S. PATENT DOCUMENTS

| 7,214,786 B2 | 5/2007 | Kovalic et al. |
| 7,612,177 B2 | 11/2009 | Mulet Salort et al. |
| 2009/0144849 A1* | 6/2009 | Lutfiyya .................. 800/278 |

OTHER PUBLICATIONS

Mazzucotelli et al., 2006, Current Genomics 7: 509-522.*
Roth et al., Virus Research 102: 97-108.*
Schopfer et al., 1979, Plant Physiology 64: 822-827.*
Ryu et al., 2010, Plant Physiology 154: 1983-1997, published Sep. 30, 2010.*
Zhang et al., 20025, Genes & Development 19: 1532-1543.*
Liu et al., "Functional analysis reveals pleiotropic effects of rice RING-H2 finger protein gene OsBIRF1 on regulation of growth and defense responses against abiotic and biotic stresses," Plant Mol Biol. 68(1-2):17-30 (2008).
International Search Report for International Patent Application No. PCT/KR2011/006187, mailed May 8, 2012 (4 pages).

* cited by examiner

*Primary Examiner* — David T Fox
*Assistant Examiner* — Bratislav Stankovic
(74) *Attorney, Agent, or Firm* — Clark & Elbing LLP; Susan M. Michaud

(57) ABSTRACT

The present invention relates to a composition for enhancing non-biological stress resistance in plants and a composition for accelerating germination. A nucleotide sequence of the present invention is involved in the resistance against the drying stresses in plants, and a transformed plant in which the nucleotide sequence is overexpressed has prominent resistance against various kinds of non-biological stress, including drought stress. In addition, the nucleotide sequence of the present invention is involved in ABA hormone sensitivity in plants, and germination is greatly improved in a plant in which the nucleotide sequence expression is suppressed. Therefore, the composition of the present invention can be useful as new functional crops regardless of the climate of the cultivation area, or as seeds for long-term storage with an increased storage period.

1 Claim, 10 Drawing Sheets

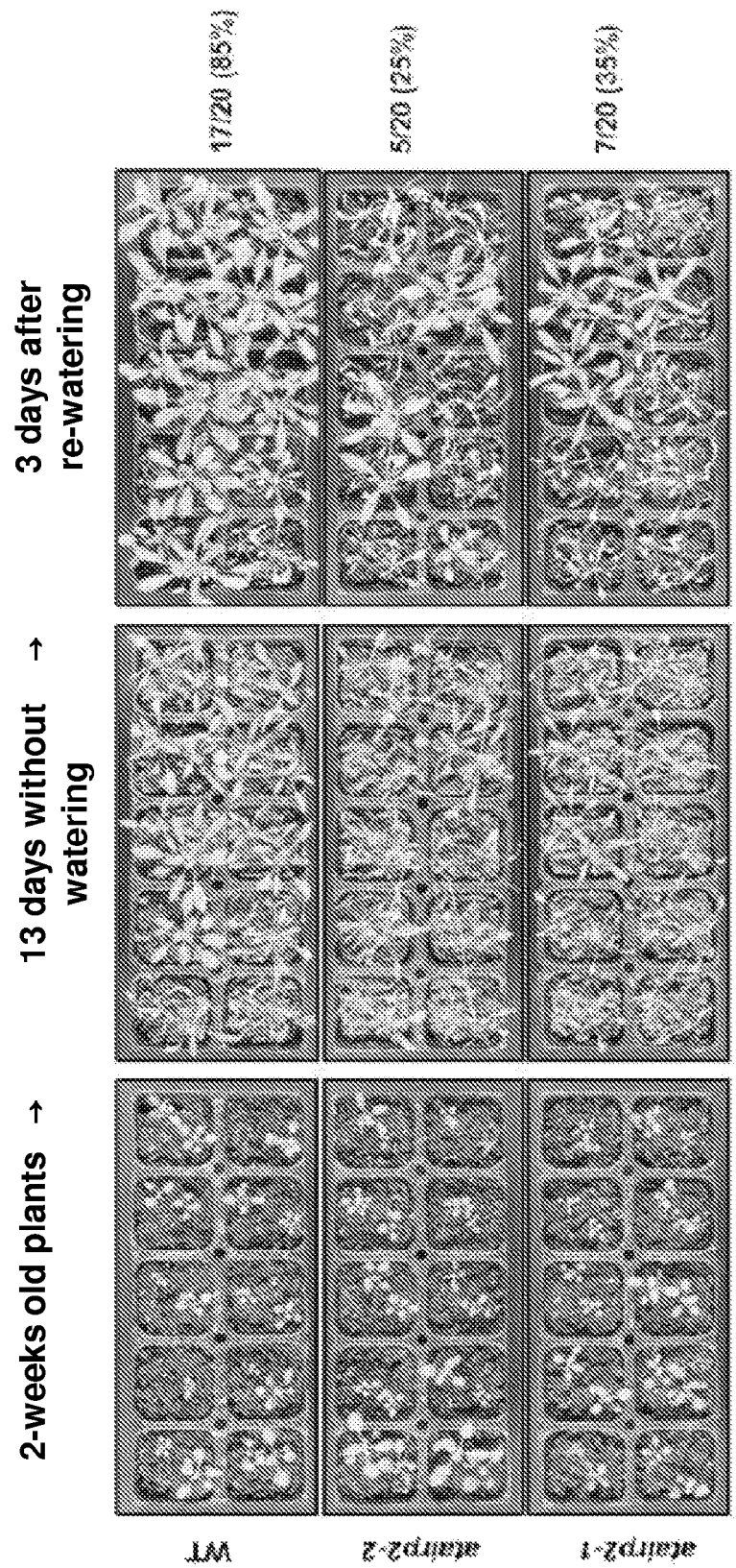

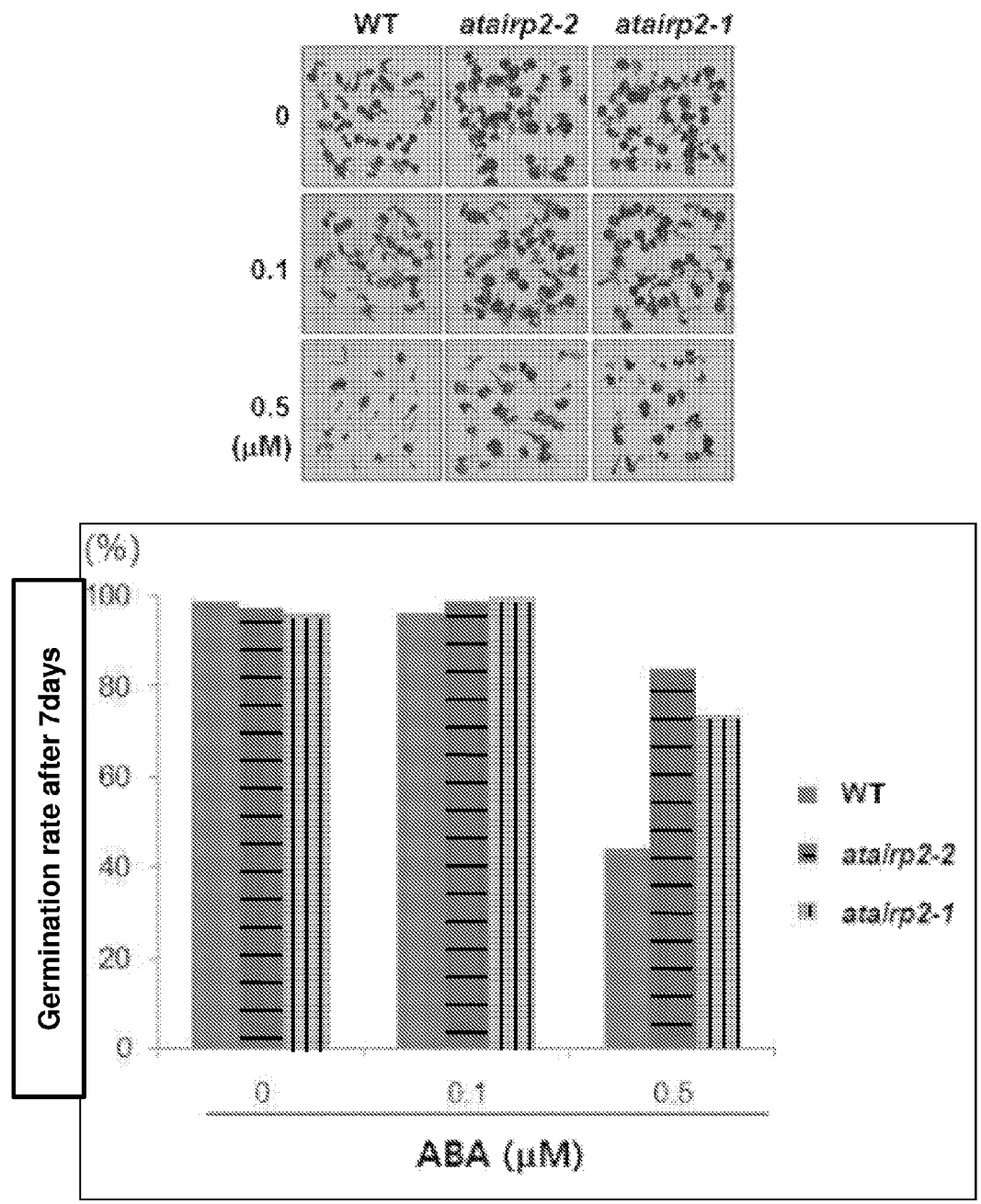

US 9,322,032 B2

ARABIDOPSIS RING E3 UBIQUITIN LIGASE FOR PROMOTION OF PLANT GERMINATION

CROSS-REFERENCE TO RELATED APPLICATIONS

This application is the U.S. national stage filing under 35 U.S.C. §371 of International Application PCT/KR2011/006187, filed Aug. 22, 2011, which claims priority from Korean Patent Application 10-2011-0050802, filed May 27, 2011.

BACKGROUND OF THE INVENTION

1. Field of the Invention

The present invention relates to a gene implicated in abiotic stress tolerance and growth promotion and a method for improving abiotic stress tolerance and promoting growing of transformed plants with the same.

2. Description of the Related Art

Due to their sessile nature, higher plants are constantly faced with various adverse environmental factors, including drought, high salt, heavy metals, cold, heat shock, and ozone, during their whole life span. These abiotic stresses are a limiting factor for the growth and development of crop plants. Water deficiency causes dramatic reduction of crop production globally, and the decreasing availability of fresh water may pose a future threat to humans and higher plants. Plants have diverse defense strategies to enhance their tolerance to transient and long-term water shortages by triggering signaling network pathways and inducing stress-responsive genes. The cellular and genetic defense mechanisms in response to water stress have been widely documented (Shinozaki and Yamaguchi-Shinozaki, 2007). However, for stress tolerance or sensitivity, our knowledge concerning the biological functions of stress-related genes in higher plants is still rudimentary. Therefore, it is important to study the functions of stress responsive genes to increase the productivity and distribution of crop plants.

Ubiquitin is a protein consisting of 76 amino acids and it has been found in almost all tissues of eukaryotic organisms. Ubiquitin has a characteristic that is covalently bound to various substrate proteins by E1-E2-E3 consecutive actions of ubiquitin-activating enzymes (E1s), ubiquitin-conjugating enzymes (E2s) and ubiquitin ligases (E3s). The substrate proteins to be attached with ubiquitin are very diverse, affecting almost all physiological activities. In addition, many studies have been found that the many diseases are associated with these mechanisms. A function of ubiquitin is firstly known to promote degradation of protein by attaching with other proteins. However, other functions of ubiquitin have been recently revealed one after another.

Ubiquitin is attached to substrate by consecutive actions of three types of proteins, i.e., E1, E2 and E3. The glycine residue at the C-terminal domain of ubiquitin binds to $NH_3$ at R— group of lysine residues on the substrate protein, thereby forming a covalent bond with the substrate. In general, proteins attached with ubiquitin are degraded by proteasome. Polyubiquitin as a chain of several ubiquitin molecules has to be attached to the substrate for degradation by proteasome. Until now, it has been known that proteasome-dependent degradation of the substrate occurs only when polyubiquitin consisting of at least four ubiquitins is attached to the substrate; however, it would be controversial since these results were obtained from in vitro experiments. Polyubiquitination leading to the proteasome-dependent degradation is the linkage form in which the $48^{th}$ lysine residue of one ubiquitin is linked to another ubiquitin.

There are 2 types of E1 enzymes in organism. There are various types of E2s. In general, E2s catalyse the transfer of ubiquitin from E1 to E3 or substrate. E3s which are also known as E3 ligases catalyse the final step of the ubiquitination cascade. E3s determine specificity of the substrate to be ubiquitinated. In other words, the substrate being capable of interaction with certain E3s is specifically determined. E3 enzymes may be classified into two major types according to domains. E3 enzymes possess one of two domains: the homologous to the E6-AP carboxyl terminus (HECT) domain and the really interesting new gene (RING) domain. E3 enzymes having RING domain serves to position E2 and substrate in close proximity each other. In other words, where E2 and the substrate bind to E3, distance between ubiquitin of E2 and the substrate is formed to close sufficiently such that ubiquitin of E2 is chemically passed to the substrate. In contrast, E3 enzymes having HECT domain receive ubiquitin from E2, and then transfer it to the substrate. The At5g01520 gene codes for the protein having E3 ubiquitin ligase enzymatic activity. The ubiquitination has been known to serve diverse functions as one of the mechanism that all higher organisms as well as plants have. However, the genes involved in abiotic stresses have been unknown. The present inventors have isolated the At5g01520 genes in which the expression is induced by abiotic stresses and ABA hormone in *Arabidopsis thaliana*. Then, they have prepared At5g015265-overexpresors and knock-out mutants and analyzed their physiological phenotypes.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventors have made intensive studies to improve a tolerance to abiotic stresses of a plant. As results, they have discovered that a nucleotide sequence encoding the amino acid sequence of SEQ ID NO:2 was involved in the above-mentioned characteristic of the plant. In addition, where the gene expression was inhibited, transgenic plants having the improved tolerance to abiotic stresses may be obtained.

Accordingly, it is an object of this invention to provide a composition for improving the tolerance of a plant to an abiotic stress, and a plant cell or a plant exhibiting improved tolerance to an abiotic stress, transformed with the composition.

It is another object of this invention to provide a composition for promoting germination of a plant.

Other objects and advantages of the present invention will become apparent from the following detailed description together with the appended claims and drawings.

BRIEF DESCRIPTION OF THE DRAWINGS

FIGS. 4a-d represent results of measuring the AtAIRP2 gene mutants and their tolerance to drought stress. FIG. 4a represents the gene map that the T-DNAs were inserted to the exon (AtAIRP2-1) and the intron (AtAIRP2-2) in genomic DNA of the AtAIRP2 gene. FIG. 4b represents that T-DNA insertions were verified by PCR amplification using the T-DNA border primer and primers annealing to sites upstream and downstream of the T-DNA insertion site with the extracted genomic DNA from the knock-out mutant. FIG. 4c represents that the expression of the gene was analyzed by RT-PCR with the extracted RNA from the knock-out mutant. Based on the results, it could be demonstrated that the expression of the gene in the AtAIRP2 mutant was inhibited. FIG. 4d represents images of comparing the tolerance to drought stress in the AtAIRP2 gene mutants and the wild type *Arabidopsis thaliana*. Each of plants was grown for 2 weeks, and subjected to drought stress by withholding water for 13 days, respectively. The plants were then re-watered and monitored the number of the survived plant. As a result, mutants were less tolerant to drought stress than the wild types (FIG. 4d).

FIG. 5b represents images of comparing the tolerance to drought stress in the AtAIRP2-overexpressing transgenic and the wild type *Arabidopsis thaliana*. Each of plants was grown for 2 weeks, and subjected to drought stress by withholding water for 14 days, respectively. The plants were then re-watered and monitored the number of the survived plant. As a result, the AtAIRP2-overexpressing transgenic plants were more tolerant to drought stress than the wild types.

FIGS. 6a-b represent results of analyzing germination rates according to ABA hormone in the AtAIRP2 knock-out mutant and the AtAIRP2-overexpressing transgenic plant. FIG. 6a represents images of the wild type, the AtAIRP2-1 mutant and the AtAIRP2-2 mutant which were grown on medium supplemented with different concentrations (0.1 and 0.5 μM) of ABA hormone for 7 days. It could be understood that the germination rates of mutants which were grown on medium supplemented with ABA hormone were higher than that of the wild types. FIG. 6b represents images of the wild type, the AtAIRP2-2 mutant and the AtAIRP2-sGFP overexpressing transgenic plant which were grown on medium supplemented with different concentrations (0.2 and 0.4 μM) of ABA hormone for 7 days. It could be understood that the germination rates of the AtAIRP2 overexpressing transgenic plants which were grown on medium supplemented with ABA hormone were significantly inhibited. In addition, it could be demonstrated that the AtAIRP2-2 mutant showed the tolerant under the same condition. Therefore, it could be understood that the germination rates in the AtAIRP2-overexpressing transgenic plants were decreased by ABA hormone and the germination rate in mutant was increased by ABA hormone.

DETAILED DESCRIPTION OF THE INVENTION

Figure 1:
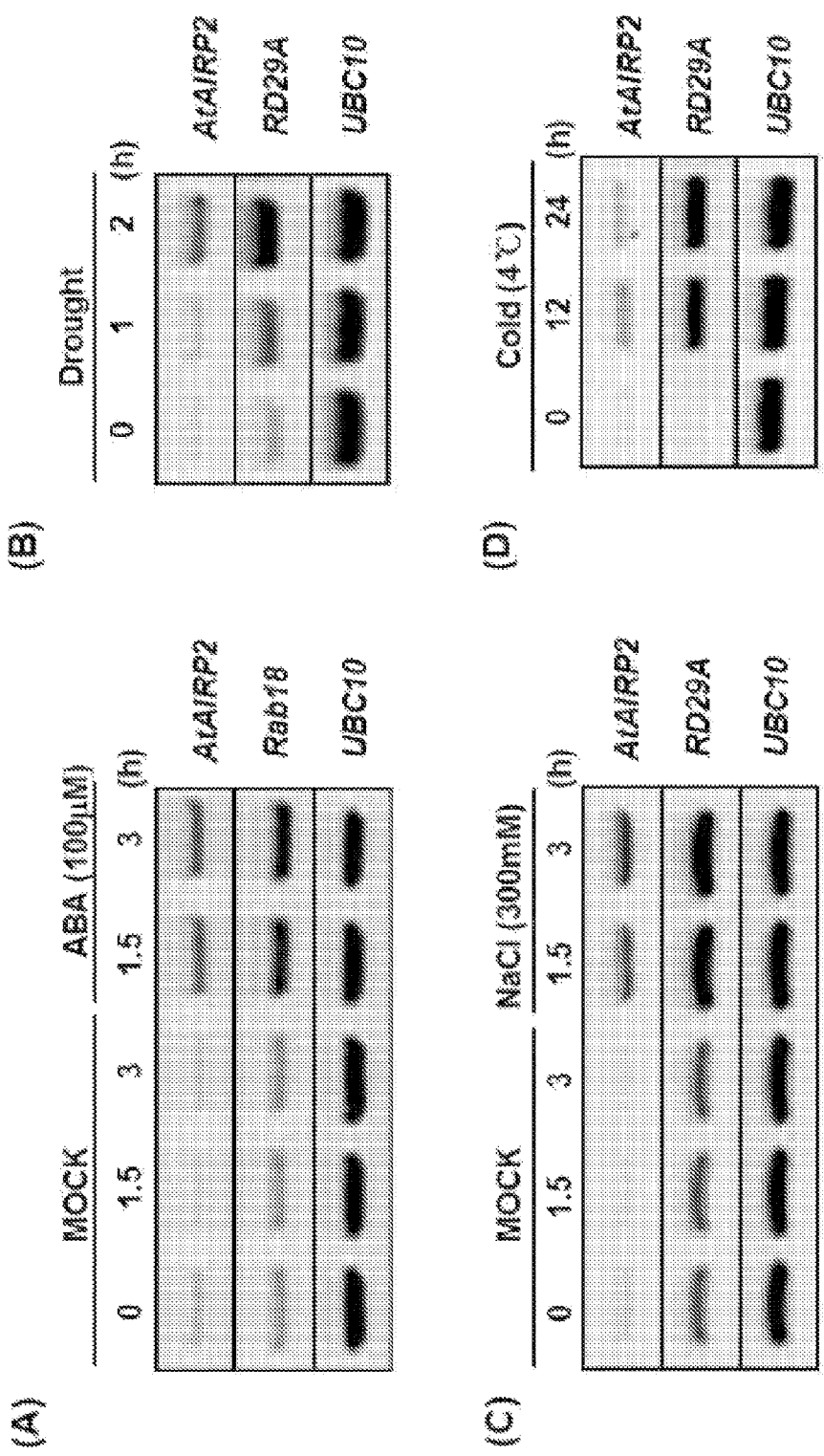
FIGS. 1a-d represent results of analyzing the AtAIRP2 gene expression by RT-PCR after treatments of various abiotic stresses and ABA hormone. After treatments of ABA hormone (FIG. 1a), drought stress (FIG. 1b), low-temperature stress (FIG. 1c) and salt stress (FIG. 1d), each RNA was extracted to analyze the gene expression pattern. RD29A was used as a representative control gene in treatments of drought, salt and low-temperature, and RAB18 was used as a representative control gene in treatment of ABA.

In one aspect of this invention, there is provided a composition for improving the tolerance of a plant to an abiotic stress, comprising a nucleotide sequence encoding the amino acid sequence of SEQ ID NO:2.

The present inventors have made intensive studies to improve a tolerance to abiotic stresses of a plant. As results, they have discovered that a nucleotide sequence encoding the amino acid sequence of SEQ ID NO:2 was involved in the above-mentioned characteristic of the plant. In addition, where the gene expression was inhibited, transgenic plants having the improved tolerance to abiotic stresses may be obtained.

According to a preferred embodiment, the present nucleotide sequence encoding the amino acid sequence of SEQ ID NO:2 comprises the nucleotide sequence as set forth in SEQ ID NO:1. According to the present invention, the nucleotide sequence as set forth in SEQ ID NO:1 is the nucleotide sequence of the At5g01520 gene in *Arabidopsis thaliana*, and the gene is named as the AtAIRP2 (*Arabidopsis thaliana* ABA Insensitive Ring Protein 2). The gene encodes RING protein having E3 ubiquitin ligase enzymatic activity. The present inventors have found that expressions of the gene were increased by various abiotic stresses and ABA hormone.

It would be obvious to the skilled artisan that the nucleotide sequences used in this invention are not limited to those listed in the appended Sequence Listings.

For nucleotides, the variations may be purely genetic, i.e., ones that do not result in changes in the protein product. This includes nucleic acids that contain functionally equivalent codons, or codons that encode the same amino acid, such as six codons for arginine or serine, or codons that encode biologically equivalent amino acids.

Considering biologically equivalent variations described hereinabove, the nucleic acid molecule of this invention may encompass sequences having substantial identity to them. Sequences having the substantial identity show at least 80%, more preferably at least 90%, most preferably at least 95% similarity to the nucleic acid molecule of this invention, as measured using one of the sequence comparison algorithms. Methods of alignment of sequences for comparison are well-known in the art. Various programs and alignment algorithms are described in: Smith and Waterman, *Adv. Appl. Math.* 2:482(1981); Needleman and Wunsch, *J. Mol. Bio.* 48:443 (1970); Pearson and Lipman, *Methods in Mol. Biol.* 24: 307-31(1988); Higgins and Sharp, *Gene* 73:237-44(1988); Higgins and Sharp, *CABIOS* 5:151-3(1989) Corpet et al., *Nuc. Acids Res.* 16:10881-90(1988) Huang et al., *Comp. Appl. BioSci.* 8:155-65(1992) and Pearson et al., *Meth. Mol. BioL* 24:307-31(1994). The NCBI Basic Local Alignment Search Tool (BLAST®) [Altschul et al., *J. Mol. BioL* 215:403-10 (1990)] is available from several sources, including the National Center for Biological Information (NBCI, Bethesda, Md.) and on the Internet, for use in connection with the sequence analysis programs blastp, blasm, blastx, tblastn and tblastx. It can be accessed at www.ncbi.nlm.nih.gov/BLAST/. A description of how to determine sequence identity using this program is available at www.ncbi.nlm.nih.gov/BLAST/blast_help.html.

According to a preferred embodiment, the present abiotic stress is selected from the group consisting of a drought stress, a low-temperature stress and a salt stress.

According to the present invention, the present inventors have demonstrated that expressions of the At5g01520 gene were increased when plants were subjected to drought stress, low-temperature stress or salt stress. In addition, they have demonstrated that the tolerances to these stresses were improved when the gene was over-expressed in plants.

More preferably, the present abiotic stress is drought stress.

In another aspect of this invention, there is provided a composition for improving a tolerance of a plant to an abiotic stress, comprising a recombinant plant expression vector which comprises: (a) the nucleotide sequence as disclosed in the present invention; (b) a promoter which is operatively linked to the nucleotide sequence of (a) and generates a RNA molecule in plant cells; and (c) a poly A signal sequence inducing polyadenylation at the 3'-end of the RNA molecule.

The term "operatively linked" as used herein refers to functional linkage between a nucleic acid expression control sequence (such as a promoter, signal sequence, or array of transcription factor binding sites) and a second nucleotide sequence, wherein the expression control sequence affects transcription and/or translation of the nucleic acid corresponding to the second sequence.

The vector system of this invention may be constructed in accordance with conventional techniques described in Sambrook et al., *Molecular Cloning, A Laboratory Manual*, Cold Spring Harbor Laboratory Press (2001), teachings of which are incorporated herein by reference.

The suitable promoter in the present invention includes any one commonly used in the art, for example SP6 promoter, T7 promoter, T3 promoter, PM promoter, maize-ubiquitin promoter, Cauliflower mosaic virus (CaMV)-35S promoter, Nopalin synthase (nos) promoter, Figwort mosaic virus 35S promoter, Sugarcane bacilliform virus promoter, commelina yellow mottle virus promoter, photo-inducible promoter of small subunit of Ribulose-1,5-bis-phosphate carboxylase (ss-RUBISCO), cytosolic triosphosphate isomerase (TPI) promoter in rice, adenine phosphoribosyltransferase (APRT) or octopine synthase promoter in *Arabidopsis*. Preferably, the promoter used in this invention is CaMV 35S.

According to a preferred embodiment, the poly A signal sequence inducing polyadenylation at the 3'-end includes that from the nopaline synthase gene of *Agrobacterium tumefaciens* (NOS 3' end) (Bevan et al., *Nucleic Acids Research*, 11(2):369-385 (1983)), that from the octopine synthase gene of *Agrobacterium tumefaciens*, the 3'-end of the protease inhibitor I or II genes from potato or tomato, the CaMV 35S terminator, and OCS (octopine synthase) terminator. Most preferably, the poly A signal sequence inducing polyadenylation at the 3'-end in this invention is OCS (octopine synthase) terminator.

Optionally, the present vector for plants may further carry a reporter molecule (e.g., genes for luciferase and β-glucuronidase). In addition, the vector may contain antibiotic resistant genes as selective markers (e.g., neomycin phosphotransferase gene (nptII) and hygromycin phosphotransferase gene (hpt)).

According to a preferred embodiment, the plant expression vector of this invention is *Agrobacterium* binary vectors.

The term "binary vector" as used herein, refers to a cloning vector containing two separate vector systems harboring one plasmid responsible for migration consisting of left border (LB) and right border (RB), and another plasmid for target gene-transferring. Any *Agrobacterium* suitable for expressing the nucleotide of this invention may be used, and most preferably, the transformation is carried out using *Agrobacterium tumefaciens* GV3101.

Introduction of the recombinant vector of this invention into *Agrobacterium* can be carried out by a large number of methods known to one skilled in the art. For example, particle bombardment, electroporation, transfection, lithium acetate method and heat shock method may be used. Preferably, the electroporation is used.

In still another aspect of this invention, there is provided a plant cell exhibiting improved tolerance to an abiotic stress, transformed with the composition of this invention.

In further aspect of this invention, there is provided a plant exhibiting improved tolerance to an abiotic stress, transformed with the composition of this invention.

To introduce a foreign nucleotide sequence into plant cells or plants may be performed by the methods (*Methods of Enzymology*, Vol. 153 (1987)) known to those skilled in the art. The plant may be transformed using the foreign nucleotide inserted into a carrier (e.g., vectors such as plasmid or virus) or *Agrobacterium tumefaciens* as a mediator (Chilton et al., *Cell*, 11:263:271 (1977)) and by directly inserting the foreign nucleotide into plant cells (Lorz et al., *Mol. Genet.*, 199: 178-182 (1985); the disclosure is herein incorporated by reference). For example, electroporation, microparticle bombardment, polyethylene glycol-mediated uptake may be used in the vector containing no T-DNA region.

Generally, *Agrobacterium*-mediated transformation is the most preferable (U.S. Pat. Nos. 5,004,863, 5,349,124 and 5,416,011), and the skilled artisan can incubate or culture the transformed cells or seeds to mature plants in appropriate conditions.

The term "plant(s)" as used herein, is understood by a meaning including a plant cell, a plant tissue and a plant seed as well as a mature plant.

The plants applicable of the present invention include, but not limited to, food crops such as rice plant, wheat, barley, corn, bean, potato, Indian bean, oat and Indian millet; vegetable crops such as *Arabidopsis* sp., Chinese cabbage, radish, red pepper, strawberry, tomato, watermelon, cucumber, cabbage, melon, pumpkin, welsh onion, onion and carrot; crops for special use such as ginseng, tobacco plant, cotton plant, sesame, sugar cane, sugar beet, *Perilla* sp., peanut and rape; fruit trees such as apple tree, pear tree, jujube tree, peach tree, kiwi fruit tree, grape tree, citrus fruit tree, persimmon tree, plum tree, apricot tree and banana tree; flowering crops such as rose, gladiolus, gerbera, carnation, chrysanthemum, lily and tulip; and fodder crops such as ryegrass, red clover, orchardgrass, alfalfa, tallfescue and perennial ryograss.

In still further aspect of this invention, there is provided a composition for promoting germination of a plant comprising a nucleic acid molecule, wherein nucleic acid molecule inhibits an expression of a nucleotide sequence encoding the amino acid sequence of SEQ ID NO:2.

According to a preferred embodiment, the present nucleotide sequence comprises the nucleotide sequence as set forth in SEQ ID NO:1.

According to the present invention, the nucleotide sequence as set forth in SEQ ID NO:1 is the nucleotide sequence of the At5g01520 gene. According to the present invention, it was determined that Where expressions of the present nucleotide sequence were inhibited, the sensitivity to ABA hormone suppressing immature-germination was decreased such that the germination rates were increased. Therefore, the present nucleic acid molecule enables to store seeds for a long time with excellent germination rates.

According to a preferred embodiment, the nucleic acid molecule is T-DNA, siRNA, shRNA, miRNA, ribozyme, PNA (peptide nucleic acids) or antisense oligonucleotide. More preferably, the present nucleic acid molecule is T-DNA.

The term "siRNA" used herein refers to a short double strand RNA that enables to mediate RNA interference via cleavage of mRNA. The siRNA of the present invention may consist of a sense RNA strand having a sequence corresponding to a target gene and an antisense RNA strand having a sequence complementary to the target gene. The siRNA to inhibit expression of a target gene provides effective gene knock-down method or gene therapy method.

The siRNA of this invention is not restricted to a RNA duplex of which two strands are completely paired and may comprise non-paired portion such as mismatched portion with non-complementary bases and bulge with no opposite bases. The overall length of the siRNA is 10-100 nucleotides, preferably 15-80 nucleotides, and more preferably, 20-70 nucleotides. The siRNA may comprise either blunt or cohesive end so long as it enables to inhibit the target gene expression via RNAi effect. The cohesive end may be prepared in 3'-end overhanging structure or 5'-end overhanging structure. The base number protruded is not particularly limited, for example 1-8 bases, preferably 2-6 bases. In addition, siRNA may comprise low molecular weight RNA (for example, tRNA, rRNA, natural RNA molecule such as viral RNA or artificial RNA molecule) in the protruded portion of one end to the extent that it enables to maintain an effect on the inhibition of target gene expression. The terminal structure of siRNA is not demanded as cut structure at both ends, and one end portion of double strand RNA may be stem-and-loop structure linked by a linker RNA. The length of linker is not restricted where it has no influence on the pair formation of the stem portion.

The term "shRNA" used herein refers to a single strand nucleotide consisting of 50-70 bases, and forms stem-loop structure in vivo. Long RNA of 19-29 nucleotides is complementarily base-paired at both directions of loop consisting of 5-10 nucleotides, forming a double-stranded stem.

The term "miRNA (microRNA)" functions to regulate gene expression and means a single strand RNA molecule composed of 20-50 nucleotides in full-length, preferably 20-45 nucleotides, more preferably 20-40 nucleotides, much more preferably 20-30 nucleotides and most preferably, 21-23 nucleotides. The miRNA is an oligonucleotide which is not expressed intracellularly, and forms a short stem-loop structure. The miRNA has a whole or partial complementarity to one or two or more mRNAs (messenger RNAs), and the target gene expression is suppressed by the complementary binding of miRNA to the mRNA thereof.

The term used herein "ribozyme" refers to a RNA molecule having an activity of an enzyme in itself which recognizes and restricts a base sequence of a specific RNA. The ribozyme consists of a binding portion capable of specifically binding a base sequence complementary to a transfer RNA strand and an enzymatic portion to cut target RNA.

The term "PNA (peptide nucleic acid)" used herein refers to a molecule having the characteristics of both nucleic acid and protein, which is capable of complementarily binding to DNA or RNA. PNA was first reported in 1999 as similar DNA in which nucleobases are linked via a peptide bond (Nielsen P E, Egholm M, Berg R H, Buchardt O, "Sequence-selective recognition of DNA by strand displacement with a thymine-substituted polyamide", Science 1991, Vol. 254: pp 1497-1500). PNA is absent in the natural world and artificially synthesized through a chemical method. PNA is reacted with a natural nucleic acid having a complementary base sequence through hybridization response, forming double strand. In the double strand with the same length, PNA/DNA and PNA/RNA double strand are more stable than DNA/DNA and DNA/RNA double strand, respectively. The form of repeating N-(2-aminoethyl)-glycine units linked by amide bonds is commonly used as a basic peptide backbone. In this context, the backbone of peptide nucleic acid is electrically neutral in comparison to that of natural nucleic acids having negative charge. Four bases of nucleic acid present in PNA are almost the same to those of natural nucleic acid in the respect of spatial size and distance between nucleobases. PNA has not only a chemical stability compared with natural nucleic acid, but also a biological stability due to no degradation by a nuclease or protease.

The term "antisense oligonucleotide" used herein is intended to refer to nucleic acids, preferably, DNA, RNA or its derivatives, that are complementary to the base sequences of a target mRNA, characterized in that they bind to the target mRNA and interfere its translation to protein. The antisense oligonucleotide of the present invention refers to DNA or RNA sequences which are complementary to a target mRNA, characterized in that they bind to the target mRNA and interfere its translation to protein, translocation into cytoplasm, maturation or essential activities to other biological functions. The length of antisense nucleic acids is in a range of 6-100 nucleotides and preferably 10-40 nucleotides.

The antisense oligonucleotides may be modified at above one or more positions of base, sugar or backbone to enhance their functions [De Mesmaeker, et al., *Curr Opin Struct Biol.*, 5(3): 343-55 (1995)]. The oligonucleotide backbone may be modified with phosphothioate, phosphotriester, methyl phosphonate, single chain alkyl, cycloalkyl, single chain heteroatomic, heterocyclic bond between sugars, and so on. In addition, the antisense nucleic acids may include one or more substituted sugar moieties. The antisense oligonucleotides may include a modified base. The modified base includes hypoxanthine, 6-methyladenine, 5-me pyrimidine (particularly, 5-methylcytosine), 5-hydroxymethylcytosine (HMC), glycosyl HMC, gentobiosyl HMC, 2-aminoadenine, 2-thiouracil, 2-thiothymine, 5-bromouracil, 5-hydroxymethyluracil, 8-azaguanine, 7-deazaguanine, N6(6-aminohexyl)adenine, 2,6-diaminopurine, and so forth.

The term "T-DNA" used herein refers to a DNA fragment as a transfer DNA in Ti (tumor-inducing) plasmid of *Agrobacterium* sp., which is transferred into a nucleus of a host plant cell. A 25 bp repeat sequence is present in both termini of T-DNA, and DNA transfer proceeds at the direction from a left border to a right border. A bacterial T-DNA with about 20,000 in length destroys a target gene by insertion, resulting in insertional muatagenesis. In addition to mutation, inserted T-DNA sequence may label a target gene. According to the present invention, the present inventors have used seeds of *Arabidopsis thaliana* for suppressing the expression of the At5g01520 gene by means of Ti-plasmid transformation.

In still further aspect of this invention, there is provided a composition for promoting germination of a plant, comprising a recombinant plant expression vector which comprises: (a) the nucleotide sequence as disclosed in the present invention; (b) a promoter which is operatively linked to the nucleotide sequence of (a) and generates a RNA molecule in plant cells; and (c) a poly A signal sequence inducing polyadenylation at the 3'-end of the RNA molecule.

Since the nucleic acid molecule, the plant expression recombinant vector and the introduction method thereof are mentioned above, they are omitted herein to avoid excessive overlaps.

The features and advantages of the present invention will be summarized as follows:

(a) The present invention provides a composition for improving the tolerance of a plant to an abiotic stress and a composition for promoting germinating of a plant.

(b) The present nucleotide sequence is involved in tolerance to drought stress of plants. Therefore, the overexpressing transgenic plants have excellent tolerances to various abiotic stresses including drought stress, whereby they may be useful as novel functional crops which are affected by climates and environments of the cultivated areas.

(c) In addition, the present nucleotide sequence is involved in sensitivity to ABA hormone of plants. Therefore, germination abilities of the knock-out mutant plants in which the expression is inhibited are remarkably enhanced, whereby they may effectively used for cultivating the plants with novel function of storage period increasing, and biomass.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experimental Methods
Isolation of the Genes

The present inventors have isolated the AtAIRP2 genes inducible by ABA hormone and abiotic stresses from cDNAs of *Arabidopsis thaliana*. 10-day-old *Arabidopsis thaliana* seedlings were grinded with liquid nitrogen in mortar. The powders were added with 2 ml of an extraction buffer (4 M guanidine-HCl 20 mM, 10 mM EDTA, 10 mM EGTA (USB), 0.5% Sarkosyl (SIGMA), pH 9) and β-mercaptoethanol (SIGMA-ALDRICH) per 1 g of the powder for extraction. The extraction resultant was transferred to new conical tube, suspended with an equal volume of PCI (phenol:chloroform: isoamyl alcohol=25:24:1), vortexed for 5 min and centrifuged at 3,500 rpm for 25 min (Hanil centrifuge, HA-1000-3). After centrifugation, the upper organic solvent phase was removed. The extract was resuspended with an equal volume of PCI, vortexed and centrifuged twice. Then, the lower aqueous phase was undergone twice ethanol precipitation and once LiCl precipitation to isolate RNA. RNA was quantified. Single-strand cDNA was synthesized by using 2 μg of RNA with oligo dT primer and MMLV reverse transcriptase (Fermentas). PCR was conducted in the final volume of 50 μL containing 20 ng of cDNA as a template, 10 pmole of each of two types of primers, 5 μL of 10×Taq polymerase buffer (Takara), 8 μL of dNTPs (each of 1.25 mM) and 1 unit of Taq DNA polymerase (Takara). The tube containing the reaction mixture was placed in Perkin Elmer DNA thermal cycler. The sequences of primers used in this Example are as follows: 5'-ATGCGAAAATCGTTCAAGGA-3' (AtAIRP2 ORF FW: SEQ ID NO: 3) and 5'-TCACCGAGGAAGAGGAG-CATAA-3' (AtAIRP2 ORF RV: SEQ ID NO: 41). The reaction mixture was denatured for 2 min at 94° C. and subjected to 30 cycles of 30 sec at 94° C., 30 sec at 52° C. and 1 min at 72° C. After 30 cycles, polymerization was further performed at 72° C. for 5 min. Then, the AtAIRP2 gene amplification was verified by using electrophoresis method. In addition, the DNA was confirmed by sequencing.

Plant Growth Conditions and Sampling

In order to prepare the AtAIRP2-overexpressing transgenic plants, Invitrogen GATEWAY® system was used to construct. First, AtAIRP1-sGFP was introduced into pENTR SD Topo vector (invitrogen, USA) and subsequently integrated into pEarlygate 100 vector (Arabidopsis research center, USA) of plants using LR clonase enzyme (Invitrogen).

Seeds of the AtAIRP2 knock-out mutants (seed number: SAIL_686_G08 (AtAIRP2-1), Salk_005082 (AtAIRP2-2)) which are T-DNA insertion lines were purchased from SIGNAL Salk Institute Genomic Analysis Laboratory (signal.salk.edu).

The seeds of the AtAIRP2-overexpressing transgenic plants, knock-out mutants and the wild type *Arabidopsis thaliana* were soaked in 30% bleach solution (Yuhanclorox) and 0.025% Triton X-100 for 10 min, and washed 10 times with sterilized water. The treated seeds were grown on MS (Murashige and Skoog) medium (Duchefa Biochemie) that contained 3% sucrose, B5 vitamin (12 mg/L) and 0.8% agar (pH 5.7) in a growth chamber for 2 weeks (under a condition of 16 hrs-light/8 hrs-dark cycle). Where green whole plants of light condition were used as materials, seeds were grown on soil of Sunshine MIX #5 (Sun GroHorticulture) in a growth chamber for 3 weeks (under a condition of 16 hrs-light/8 hrs-dark cycle).

Treatments of Stresses (Salt, Low-Temperature, Drought and ABA Hormone)

In order to determine expressions of the AtAIRP2 gene to drought stress, the wild type *Arabidopsis thaliana* seedlings which were grown on medium for 2 weeks were exposed in the air, and sampled after 1 hour and 2 hours. In order to determine expressions of the AtAIRP2 gene to salt stress, the wild type *Arabidopsis thaliana* seedlings which were grown on medium for 2 weeks were treated with 300 mM sodium chloride, and sampled after 1.5 hour and 3 hours. In order to determine expressions of the AtAIRP2 gene to low-temperature stress, the wild type *Arabidopsis thaliana* seedlings which were grown on medium for 2 weeks were incubated at 4° C. for 12 hours and 24 hours, and sampled. In order to determine expressions of the AtAIRP2 gene to ABA hormone stress, the wild type *Arabidopsis thaliana* seedlings which were grown on medium for 2 weeks were treated with 100 μM of ABA (SIGMA), and sampled after 1.5 hour and 3 hours. The sampled tissues were grinded with liquid nitrogen in mortar. The powders were added with β-mercaptoethanol (SIGMA-ALDRICH) and 2 ml of an extraction buffer (4 M guanidine-HCl 20 mM, 10 mM EDTA, 10 mM EGTA (USB), 0.5% Sarkosyl (SIGMA), pH 9) per 1 g of the powder to extract. The extract was transferred to new conical tube, suspended with an equal volume of PCI (phenol:chloroform: isoamyl alcohol=25:24:1), vortexed for 5 min and centrifuged at 3,500 rpm for 25 min (Hanil centrifuge, HA-1000-3). After centrifugation, the supernatant which is upper organic solvent phase was removed. The extract was resuspended with an equal volume of PCI, vortexed and centrifuged. The extract was performed twice with the process described above. Then, the lower aqueous phase was performed twice with ethanol precipitation and once with LiCl precipitation to isolate RNA.

Quantitative Reverse Transcriptase Polymerase Chain Reaction (RT-PCR)

Total RNA was isolated from leaves of the AtAIRP2-overexpressing transgenic plants, knock-out mutants and the wild type *Arabidopsis thaliana*. Single-strand cDNA was synthesized by using 2 μg of RNA with oligo dT primer and MMLV reverse transcriptase (Fermentas). PCR was conducted in the final volume of 50 μL containing 20 ng of cDNA as a template, 10 pmole of each of two types of primers, 5 μL of 10×Taq polymerase buffer (Intron), 8 μL of dNTPs (each of 1.25 mM) and 1 unit of Taq DNA polymerase (Intron). The tube containing the reaction mixture was placed in Perkin Elmer DNA thermal cycler. The reaction mixture was denatured for 2 min at 94° C. and subjected to 25 cycles of 30 sec at 94° C., 30 sec at 52° C. and 1 min at 72° C. After 25 cycles, polymerization was further performed at 72° C. for 5 min. Then, the PCR products were stored at −20° C. in a freezer. The sequences of primers used in this Example are shown in Table 1.

TABLE 1

Primers used in RT-PCR

| Primer | sequence |
|---|---|
| AtAIRP2 RT FW (SEQ ID: 5) | 5'-GATGGTGGCTACGTTCAGA-3' |
| AtAIRP2 RT RV (SEQ ID: 6) | 5'-AAATGTCAATAACCAATGGTTG-3' |
| Rab18 FW (SEQ ID: 7) | 5'-GCGTCTTACCAGAACCGTCC-3' |
| Rab18 RV (SEQ ID: 8) | 5'-CCCTTCTTCTCGTGGTGC-3' |
| RD29a FW (SEQ ID: 9) | 5'-CAGGTGAATCAGGAGTTGTT-3' |
| RD29a RV (SEQ ID: 10) | 5'-CCGGAAATTTATCCTCTTCT-3' |
| UBC10 FW (SEQ ID: 11) | 5'-TGGATATGGCGTCGAAGC-3' |
| UBC10 RV (SEQ ID: 12) | 5'-GTGGGATTTTCCATTTAGCC-3' |

Extraction of Genomic DNA of Mutants Inserted with T-DNA and Acquisition of Homozygous Mutant The seeds of the wild type *Arabidopsis thaliana* and knock-out mutants were grown on soil for 2 weeks and their leave were sampled. The leaves were grinded with liquid nitrogen in mortar. The powders were added with 700 mL of CTAB buffer (2% CTAB, 100 mM Tris pH 8, 20 mM EDTA, 1.4 M NaCl, 2% PVP), mixed and heated at 65° C. for 10 min. The resultants were added to 200 mL of chloroform, mixed and centrifuged. After centrifugation, the supernatant was removed. The resultant was mixed with isopropanol to precipitate DNA. The precipitate was washed with 70% ethanol, dried. The obtained genomic DNA was dissolved in water to use. Genotyping PCR was performed using T-DNA border primer (LB_6313R) and primers annealing to sites upstream and downstream of the T-DNA insertion site.

TABLE 2

Primers used in Genotyping PCR and RT-PCR

| Primer | Sequence |
|---|---|
| LB_6313R (SEQ ID: 13) | 5'-GAGCTGCTATACACTGATCTGAG -3' |
| AtAIRP2 FW1 (SEQ ID: 14) | 5'-CGTGTGCTCTACGCGAATC-3' |
| AtAIRP2 RV1 (SEQ ID: 15) | 5'-CCCTTAATCAGCAAATATGATATCG-3' |

Figure 4A:
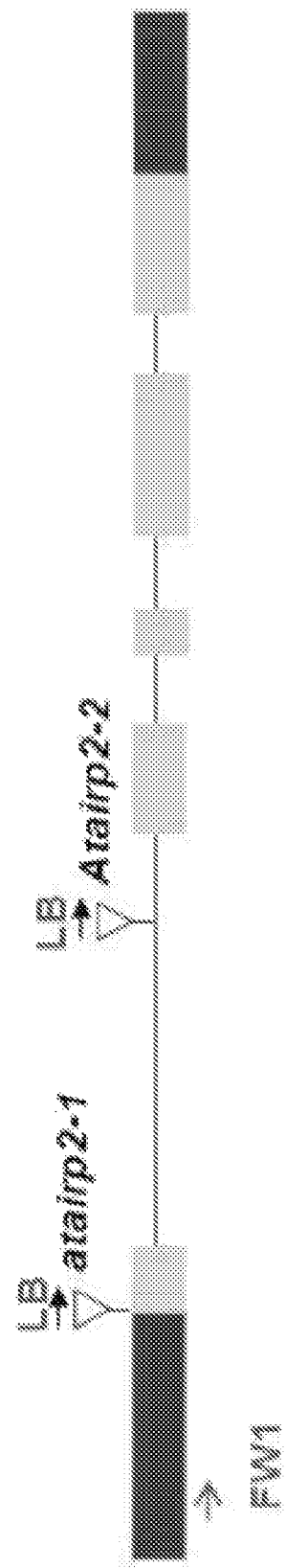
Figure 4B:
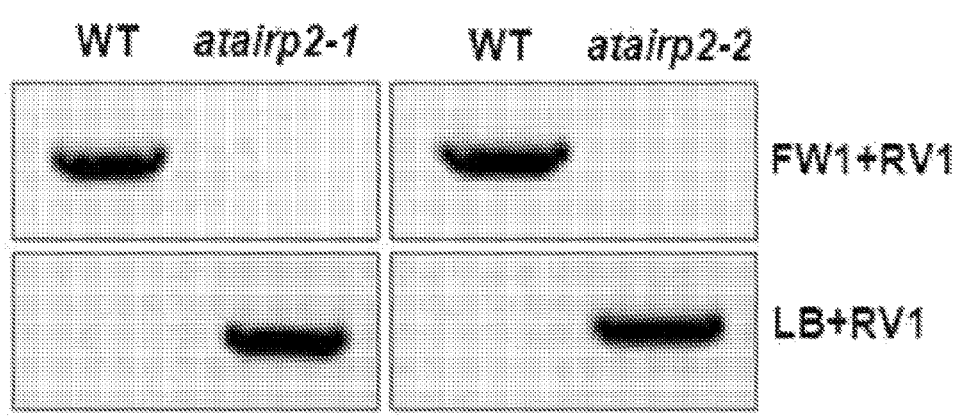
Figure 4C:
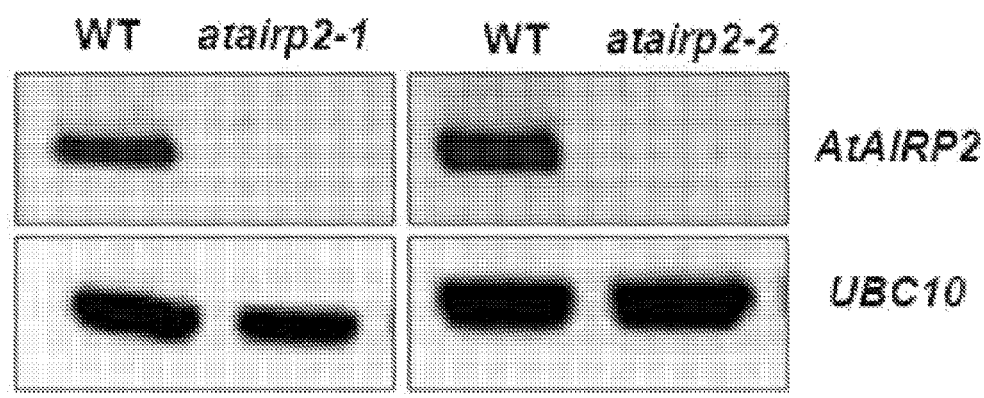

It was revealed that the T-DNA insertions were mapped to the second exon and the first intron in the AtAIRP2 gene knock-out mutant, which was verified by PCR amplification using the T-DNA border primer and primers annealing to sites upstream and downstream of the T-DNA insertion site (FIG. 4b). In addition, the suppression of the gene expression was analyzed by RT-PCR using AtAIRP2 FW1 and AtAIRP2 RV1 primers with the extracted RNA from the knock-out mutant (FIG. 4c).

Preparation of Vector Construct of the AtAIRP2 Gene

For construction of a recombinant plasmid for expressing the fusion protein between the AtAIRP2 and maltose-binding protein (MBP), PCR was carried out using a primer set designed to contain XbaI and PstI restriction sites linked to 5'-direction and 3'-direction of the coding region of the AtAIRP2 gene, respectively. PCR products and pMAL-X vector (New England Biolabs, Beverly, MA) were restricted by XbaI and PstI restriction enzymes and then ligated using T4 DNA ligase (New England Bio Lab). The recombinant MBP-AtAIRP2 was expressed in *Escherichia coli* strain BL21-CodonPlus (DE3) RIL (Stratagene) and purified using amylose column chromatography. The protein was quantified using BSA as a standard protein. In addition, in the present invention, Invitrogen GATEWAY® system was used to construct for preparing transgenic plants. First, AtAIRP2-sGFP was introduced into pENTR SD Topo vector (Invitrogen, USA) and subsequently integrated into pEarlygate 100 vector (Arabidopsis research center, USA) of plants using LR clonase enzyme (Invitrogen).

AtAIRP2 Transformation with *Agrobacterium tumefaciens* Strain and Preparation of the AtAIRP2 Transgenic Plants The prepared constructs were transferred to *Agrobacterium tumefaciens* strain GV3101 by electroporation. The presence of the gene was confirmed by PCR. An aerial part of approximately 4-week-old *Arabidopsis thaliana* (columbia [Col-0]) was soaked on MS medium (Duchefa Biochemie) containing 0.05% Silwet for 1.5 min to transform (dough and Bent, 1998, Plant J 16; 735-743). The seedlings were grown for 3 weeks in a 23° C.-growth chamber to obtain seeds (T1). The transformed seeds (T1) were selected from medium containing 25 μg/mL of BASTA (Glufosinate ammonium) and 250 μg/mL of carbenicillin. The presence of the transgene was verified by RT-PCR and western blot. Overexpression of the transgene was observed using anti-GFP antibody (clontech).

Analysis on Enzymatic Activity of the AtAIRP2 Protein

For the enzymatic activity analysis of the AtAIRP2 protein, the ORF of the AtAIRP2 gene was subcloned into pMAL-X vector in-frame with MBP (maltose-binding protein). 40 mM Tris-HCI, pH 7.5, 5 mM MgCl2, 2 mM ATP, 2 mM dithiothreitol (DTT), 300 ng/μL ubiquitin (Sigma), 25 μM MG132 (A.G. Scientific Inc.), 500 ng UBA1 (ABRC, www.arabidopsis.org), 500 ng UBC8 (ABRC, www.arabidopsis.org) and 500 ng MBP-AtAIRP2 were added to each of tubes and incubated at 30° C. After addition of sample buffer solution, the resultant was heated at 100° C. for 5min, and performed by Western blot using anti-MBP (New England Bio Labs) and anti-ubiquitin (Santa Cruz) antibodies.

Comparison of Plant Growth

For comparing phenotypes to ABA hormone, seeds obtained from the wild type, the AtAIRP2 knock-out mutant and the AtAIRP2-overexpressing transgenic plant were grown on medium supplemented with different concentrations (0, 0.2, 0.4 and 0.5 μM) of ABA hormone for 7 days, and their germination degrees were then measured. In order to compare phenotypes to salt, seeds obtained from the wild type, the AtAIRP2 knock-out mutant and the AtAIRP2-overexpressing transgenic plant were grown on medium supplemented with different concentrations (0, 0.2, 0.4 and 0.5 μM) of sodium chloride for 7 days, and their germination degrees were then measured.

Measurement of Sensitivity of Adult Plants to Drought Stress

Seeds obtained from the wild type, the AtAIRP2 knock-out mutant and the AtAIRP2-overexpressing transgenic plant were grown on soil for 2 weeks, and subjected to drought stress by withholding water for 13 or 14 days, respectively. The plants were then re-watered and measured the degrees of the tolerance to drought stress.

Histochemical GUS Assay

The wild type Arabidopsis thaliana was grown on medium for 10 days, subjected to 100 mM of ABA hormone and drought stress, and fixed with 90% acetone for 5 min. After removal of the acetone, the plant was washed 3 times with rincing solution containing 50 mM NaPO$_4$, 1 mM K$_3$Fe(CN)$_6$, and 1 mM K$_4$Fe(CN)$_6$, and immersed in 2 mM X-Gluc (5-bromo-4-chloro-3-indolyl glucuronide, sigma) and vacuumed for 1 min. After staining at 37° C. in the dark until the color was changed, the plant was incubated in 90% ethanol to remove chlorophyll.

Experimental Results

The AtAIRP2 Gene Expression after Stress Treatments (Salt, Low-temperature and Drought)

Figure 2:
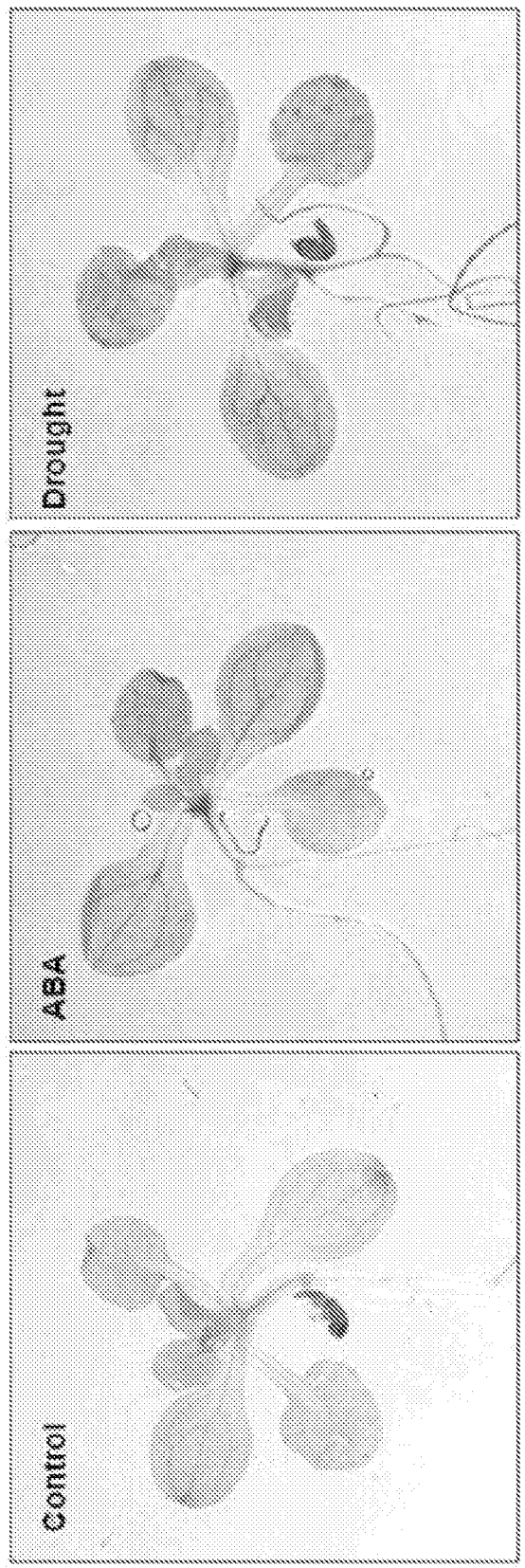
FIG. 2 represents results of analyzing the promoter activity of the AtAIRP2 gene by GUS assay. When 100 μM ABA (3 hours) or drought (2 hours) condition was treated, GUS signals were markedly induced. It could be determined that promoter activity of the AtAIRP2 gene was increased.

The AtAIRP2 gene expressions in various abiotic stresses were analyzed by RT-PCR. After treatments of low-temperature (12 hours and 24 hours), drought (1 hour and 2 hours), salt (1.5 hour and 3 hours) and ABA hormone (1.5 hour and 3 hours) stresses, RNA from each of samples was extracted to analyze the gene expression patterns. As a result, it was determined that the gene expression levels of stress treatments were increased than those of non-stress treatments, thereby the AtAIRP2 gene expression is induced by salt, low-temperature, drought and ABA hormone stresses (FIG. 1). In addition, the AtAIRP2 protein expressions in various abiotic stresses were analyzed by histochemical GUS assay. After treatments of ABA hormone (3 hours) and drought (2 hours) stresses, the degree of the staining was analyzed. As a result, it was determined that the degrees of the staining of stress treatments were increased than those of before the stress treatments (FIG. 2).

Analysis on Enzymatic Activity of the AtAIRP2 Protein

Figure 3:
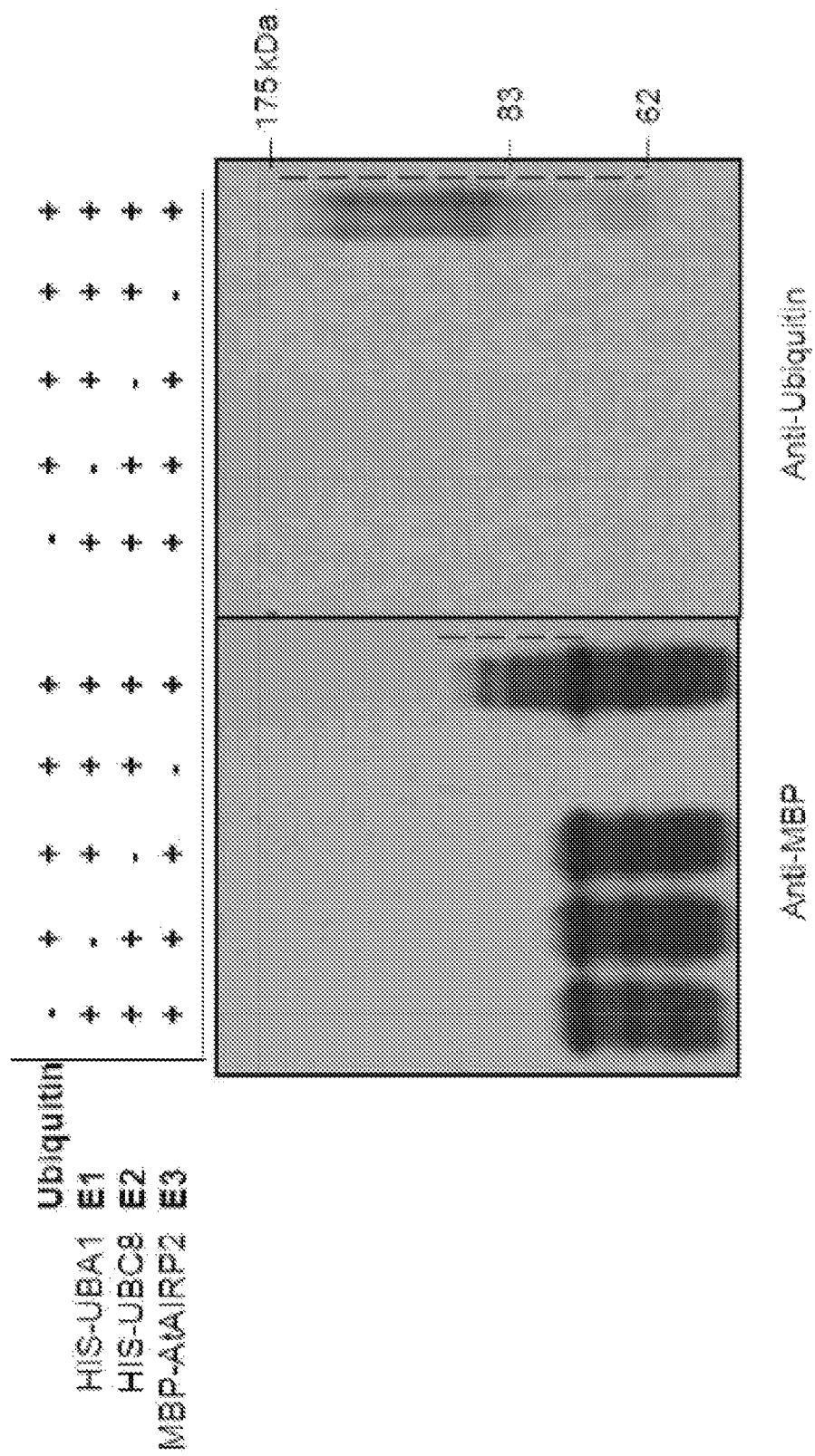
FIG. 3 represents results of analyzing the enzymatic activity of the AtAIRP2 protein. Maltose-binding protein (MBP) was bound to the AtAIRP2 proteins. Then, MBP-AtAIRP2 was incubated with HIS-UBA1, HIS-UBC8, ubiquitin and AtAIRP2 at 30° C. for 1 hour to perform Self-Ubiquitination, and performed by Western blot using MBP- and ubiquitin-specific antibodies to analyze changes in the protein levels. As a result, it was determined that the molecular weight of the AtAIRP2 protein was increased through Western blot using anti-MBP antibody, and the increase was induced due to ubiquitin. Based on the results, it could be demonstrated that the AtAIRP2 protein possessed ability for enzymatic activity of E3 ubiquitin ligase that binds ubiquitin protein.

Maltose-binding protein (MBP) was bound to the AtAIRP2 proteins. Then, the MBP-AtAIRP2 was incubated with UBA1, UBC8, ubiquitin and AtAIRP2 at 30° C. for 1 hour to perform Self-Ubiquitination, and performed by Western blot using MBP- and ubiquitin-specific antibodies to analyze changes in the protein levels. As a result, it was determined that the molecular weight of the AtAIRP2 protein was increased through Western blot using anti-MBP antibody, and the increase was induced due to ubiquitin (FIG. 3). Based on the results, it could be demonstrated that the AtAIRP2 protein possessed ability for enzymatic activity of ligase that binds ubiquitin protein.

Acquisition of the AtAIRP2 Mutants

As shown in FIG. 4a, the gene that the T-DNA insertions were mapped to the second exon and the first intron was used in order to prepare the mutants. In order to determine whether to insert and position of T-DNA, genotyping PCR was performed using T-DNA boder primer and primers annealing to sites upstream and downstream of the T-DNA insertion site. As a result, it was determined that T-DNA was inserted in the same direction as that of the gene (FIG. 4b). In addition, in order to determine whether to express mRNA of the full-length AtAIRP2 gene in mutants, the same primers used in genotyping PCR were used. As a result, it was determined that the AtAIRP2 gene was not expressed (FIG. 4c).

Measurement of Sensitivity of Adult Plants to Drought Stress

Figure 5A:
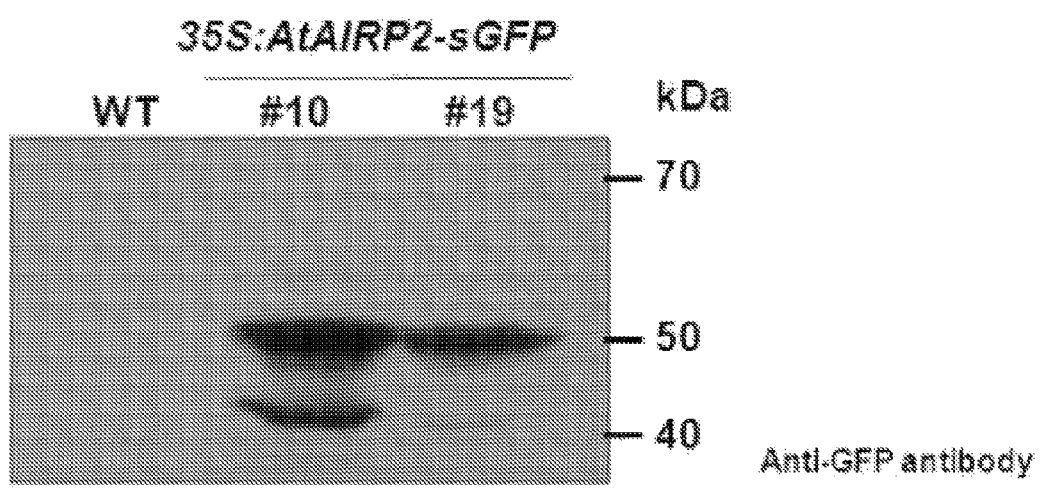
FIGS. 5a-b represent results of the AtAIRP2-overexpressing transgenic plants. *Arabidopsis thaliana* was transformed by 355:AtAIRP2-GFP recombinant vector and it was verified whether to overexpress the gene using anti-GFP antibody (FIG. 5a). As a result of Western blot, it could be demonstrated that the AtAIRP2-GFP protein was well-expressed.
Figure 5B:
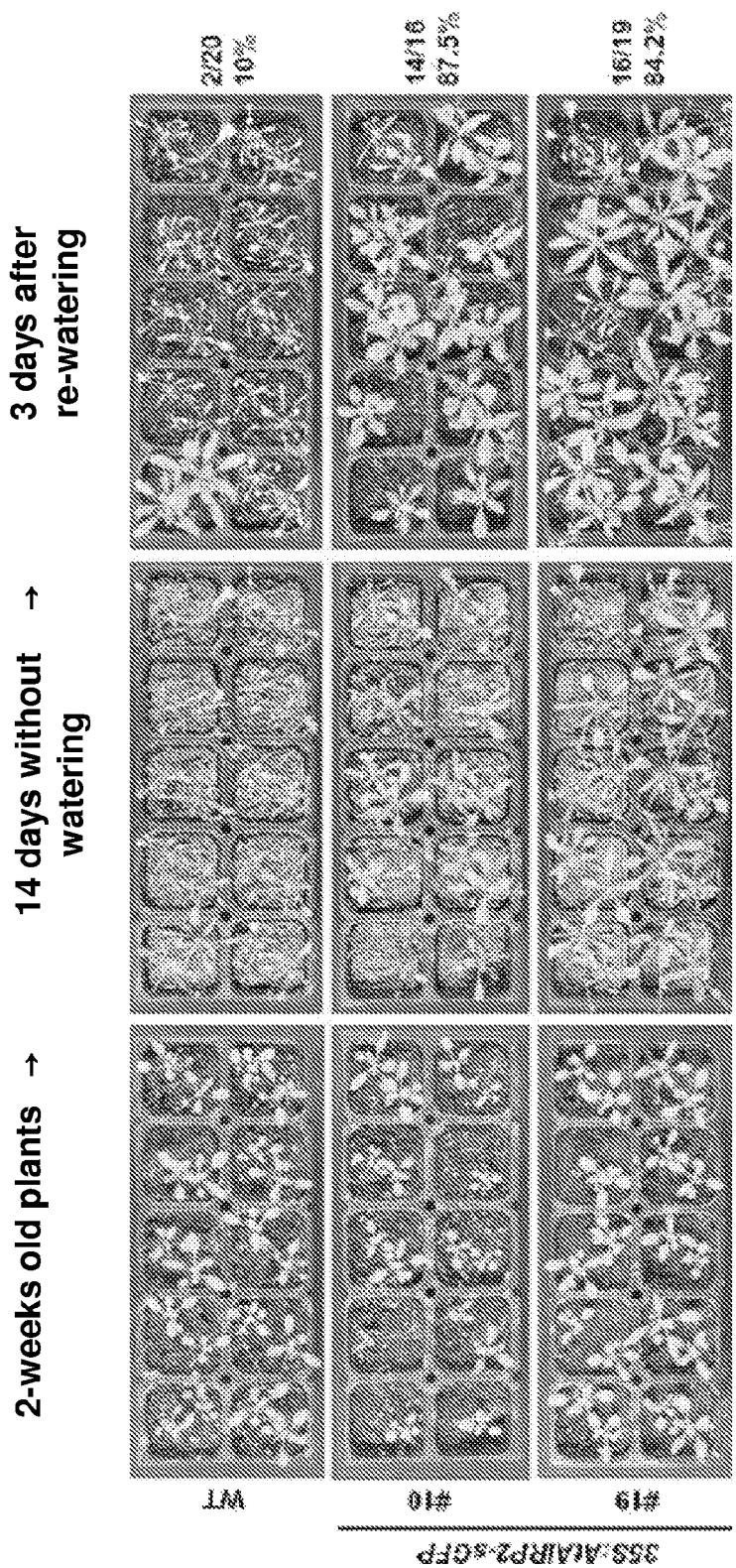

In order to measure the tolerance to drought stress in the AtAIRP2 knock-out mutant and the wild type Arabidopsis thaliana, each of the plants was grown for 2 weeks, and subjected to drought stress by withholding water for 13 days, respectively. The plants were then re-watered and monitored the number of the survived plant. As a result, knock-out mutants survived respectively by 25% and 35% whereas the wild types survived by 85%. Therefore, it could be demonstrated that the mutants were less tolerant to drought stress than the wild types (FIG. 4d). In order to measure the tolerance to drought stress in the AtAIRP2-overexpressing transgenic plants, homozygous plants of each of transgenic plants obtained through Basta selection were acquired. The obtained seeds were grown on medium. The protein expressions in transgenic plants of #10 and #19 were verified by Western Blot using anti-GFP (FIG. 5a). In order to compare the tolerance to drought stress on the AtAIRP2-overexpressing transgenic plant and the wild type Arabidopsis thaliana, each of the plants was grown for 2 weeks, and subjected to drought stress by withholding water for 14 days, respectively. The plants were then re-watered and monitored the number of the survived plant. As a result, the AtAIRP2-overexpressing transgenic plant #10 and #19 survived respectively by 87.5% and 84.2% whereas the wild types survived by 10%. Therefore, it could be demonstrated that the transgenic plants were more tolerant to drought stress than the wild types (FIG. 5b).

Comparison of Plant Germination Rate

Figure 6B:
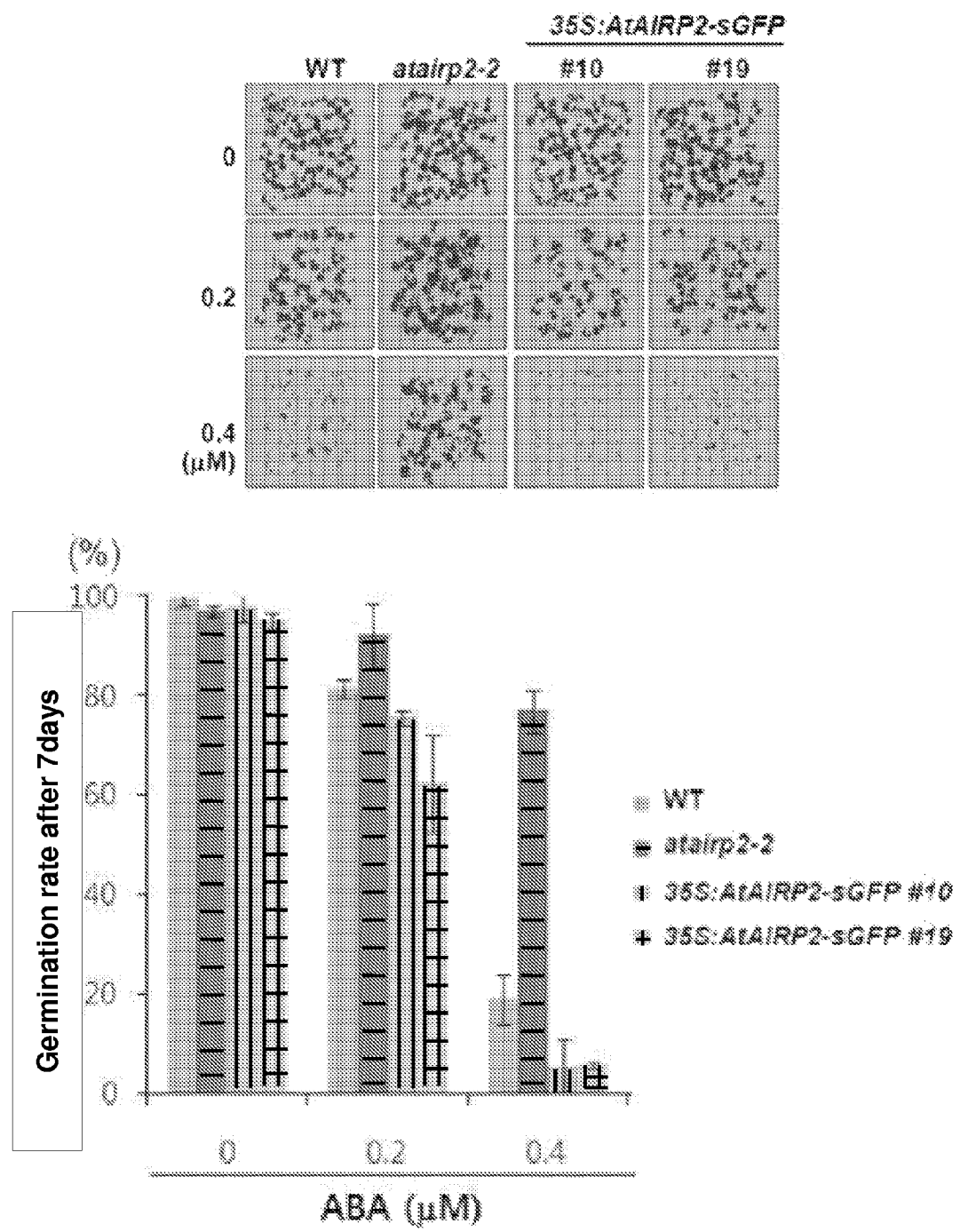

As a result of comparison on germination rate in the wild type and the AtAIRP2 knock-out mutant which were grown on medium supplemented with different concentrations (0, 0.1 and 0.5 μM) of ABA hormone for 7 days, it could be understood that the mutant showed the tolerant (FIG. 6a). As a result of comparison on germination rate in the wild type, the AtAIRP2 knock-out mutant and the AtAIRP2-overexpressing transgenic plant which were grown on medium supplemented with different concentrations (0, 0.2 and 0.4 μM) of ABA hormone for 7 days, it could be understood that the germination rates in the AtAIRP2-overexpressing transgenic plants were decreased by ABA hormone and the germination rate in the AtAIRP2 knock-out mutant was increased by ABA hormone (FIG. 6b).

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

What is claimed is:

1. A method for promoting germination of *Arabidopsis thaliana*, the method comprising:
   (a) introducing into a cell of *Arabidopsis thaliana* a nucleic acid molecule capable of inhibiting the expression of a nucleotide sequence as set forth in SEQ ID NO:1, wherein the nucleic acid molecule is T-DNA (transfer DNA) that is introduced into the nucleotide sequence as set forth in SEQ ID NO:1;
   (b) obtaining, from the cell of the *Arabidopsis thaliana*, a transgenic plant; and
   (c) growing transgenic seed obtained from said transgenic plant in the presence of abscisic acid (ABA);
   wherein the germination of the transgenic seed is improved relative to germination of wild type seed, when grown in the presence of ABA.

* * * * *

SEQUENCE LISTING

<160> NUMBER OF SEQ ID NOS: 15

<210> SEQ ID NO 1
<211> LENGTH: 729
<212> TYPE: DNA
<213> ORGANISM: Arabidopsis thaliana

<400> SEQUENCE: 1

-continued

```
atgcgaaaat cgttcaagga ttcactcaag gctcttgaag ctgatatcca gttcgccaac    60
actctggcgt cagagtaccc agaggagtat gatggtggct acgttcagat gagattatct   120
tacagcccgg cggctcatct ctttctcttc cttcttcagt ggactgattg tcatttcgct   180
ggcgctttgg gcttgcttag gatccttatt tataaggcat atgttgatgg aagaccaca    240
atgtcgctac atgaacgcaa aactagtatc agagaattct atgatgtgtt gtttccttcg   300
ctattgcaac ttcatggagg gatcaccgat gtagaagaaa ggaaacagaa ggagatatgc   360
gacaaaagat accgtaaaaa ggacagaaca gataaggaa agatgtcgga gatcgatttg    420
gagagggaag aagagtgtgg aatctgcttg gagattcgaa acaaagttgt tcttcctacg   480
tgcaatcact ccatgtgtat aaactgctac agaaactggc gtgcacggtc acagtcgtgc   540
ccgttctgtc gaggcagctt gaaaagagtg aattctggtg atctatggat atacacttgt   600
agcgccgaga ttgcagattt accagcgatt tacaaggaga tctgaagag gttgttgata    660
tacattgaca agttgcctct cgttacttct gatccaaatc ttgtcccta tgctcctctt    720
cctcggtga                                                           729
```

<210> SEQ ID NO 2
<211> LENGTH: 242
<212> TYPE: PRT
<213> ORGANISM: Arabidopsis thaliana

<400> SEQUENCE: 2

```
Met Arg Lys Ser Phe Lys Asp Ser Leu Lys Ala Leu Glu Ala Asp Ile
1               5                   10                  15

Gln Phe Ala Asn Thr Leu Ala Ser Glu Tyr Pro Glu Glu Tyr Asp Gly
            20                  25                  30

Gly Tyr Val Gln Met Arg Leu Ser Tyr Ser Pro Ala Ala His Leu Phe
        35                  40                  45

Leu Phe Leu Leu Gln Trp Thr Asp Cys His Phe Ala Gly Ala Leu Gly
    50                  55                  60

Leu Leu Arg Ile Leu Ile Tyr Lys Ala Tyr Val Asp Gly Lys Thr Thr
65                  70                  75                  80

Met Ser Leu His Glu Arg Lys Thr Ser Ile Arg Glu Phe Tyr Asp Val
                85                  90                  95

Leu Phe Pro Ser Leu Leu Gln Leu His Gly Gly Ile Thr Asp Val Glu
            100                 105                 110

Glu Arg Lys Gln Lys Glu Ile Cys Asp Lys Arg Tyr Arg Lys Lys Asp
        115                 120                 125

Arg Thr Asp Lys Gly Lys Met Ser Glu Ile Asp Leu Glu Arg Glu Glu
    130                 135                 140

Glu Cys Gly Ile Cys Leu Glu Ile Arg Asn Lys Val Val Leu Pro Thr
145                 150                 155                 160

Cys Asn His Ser Met Cys Ile Asn Cys Tyr Arg Asn Trp Arg Ala Arg
                165                 170                 175

Ser Gln Ser Cys Pro Phe Cys Arg Gly Ser Leu Lys Arg Val Asn Ser
            180                 185                 190

Gly Asp Leu Trp Ile Tyr Thr Cys Ser Ala Glu Ile Ala Asp Leu Pro
        195                 200                 205

Ala Ile Tyr Lys Glu Asn Leu Lys Arg Leu Leu Ile Tyr Ile Asp Lys
    210                 215                 220

Leu Pro Leu Val Thr Ser Asp Pro Asn Leu Val Pro Tyr Ala Pro Leu
225                 230                 235                 240
```

Pro Arg

<210> SEQ ID NO 3
<211> LENGTH: 20
<212> TYPE: DNA
<213> ORGANISM: Artificial Sequence
<220> FEATURE:
<223> OTHER INFORMATION: AtAIRP2 ORF FW primer

<400> SEQUENCE: 3
atgcgaaaat cgttcaagga                    20

<210> SEQ ID NO 4
<211> LENGTH: 22
<212> TYPE: DNA
<213> ORGANISM: Artificial Sequence
<220> FEATURE:
<223> OTHER INFORMATION: AtAIRP2 ORF RV primer

<400> SEQUENCE: 4
tcaccgagga agaggagcat aa                 22

<210> SEQ ID NO 5
<211> LENGTH: 19
<212> TYPE: DNA
<213> ORGANISM: Artificial Sequence
<220> FEATURE:
<223> OTHER INFORMATION: AtAIRP2 RT FW primer

<400> SEQUENCE: 5
gatggtggct acgttcaga                     19

<210> SEQ ID NO 6
<211> LENGTH: 22
<212> TYPE: DNA
<213> ORGANISM: Artificial Sequence
<220> FEATURE:
<223> OTHER INFORMATION: AtAIRP2 RT RV primer

<400> SEQUENCE: 6
aaatgtcaat aaccaatggt tg                 22

<210> SEQ ID NO 7
<211> LENGTH: 20
<212> TYPE: DNA
<213> ORGANISM: Artificial Sequence
<220> FEATURE:
<223> OTHER INFORMATION: Rab18 FW primer

<400> SEQUENCE: 7
gcgtcttacc agaaccgtcc                    20

<210> SEQ ID NO 8
<211> LENGTH: 18
<212> TYPE: DNA
<213> ORGANISM: Artificial Sequence
<220> FEATURE:
<223> OTHER INFORMATION: Rab18 RV primer

<400> SEQUENCE: 8
cccttcttct cgtggtgc                      18

<210> SEQ ID NO 9
<211> LENGTH: 20
<212> TYPE: DNA
<213> ORGANISM: Artificial Sequence
<220> FEATURE:
<223> OTHER INFORMATION: RD29a FW primer

<400> SEQUENCE: 9
caggtgaatc aggagttgtt                                               20

<210> SEQ ID NO 10
<211> LENGTH: 20
<212> TYPE: DNA
<213> ORGANISM: Artificial Sequence
<220> FEATURE:
<223> OTHER INFORMATION: RD29a RV primer

<400> SEQUENCE: 10
ccggaaattt atcctcttct                                               20

<210> SEQ ID NO 11
<211> LENGTH: 18
<212> TYPE: DNA
<213> ORGANISM: Artificial Sequence
<220> FEATURE:
<223> OTHER INFORMATION: UBC10 FW primer

<400> SEQUENCE: 11
tggatatggc gtcgaagc                                                 18

<210> SEQ ID NO 12
<211> LENGTH: 20
<212> TYPE: DNA
<213> ORGANISM: Artificial Sequence
<220> FEATURE:
<223> OTHER INFORMATION: UBC10 RV primer

<400> SEQUENCE: 12
gtgggatttt ccatttagcc                                               20

<210> SEQ ID NO 13
<211> LENGTH: 23
<212> TYPE: DNA
<213> ORGANISM: Artificial Sequence
<220> FEATURE:
<223> OTHER INFORMATION: LB_6313R primer

<400> SEQUENCE: 13
gagctgctat acactgatct gag                                           23

<210> SEQ ID NO 14
<211> LENGTH: 19
<212> TYPE: DNA
<213> ORGANISM: Artificial Sequence
<220> FEATURE:
<223> OTHER INFORMATION: AtAIRP2 FW1 primer

<400> SEQUENCE: 14
cgtgtgctct acgcgaatc                                                19

<210> SEQ ID NO 15
<211> LENGTH: 25
<212> TYPE: DNA
<213> ORGANISM: Artificial Sequence
<220> FEATURE:
<223> OTHER INFORMATION: AtAIRP2 RV1 primer

<400> SEQUENCE: 15
cccttaatca gcaaatatga tatcg                                         25